United States Patent [19]

Bartke

[11] 4,311,393

[45] Jan. 19, 1982

[54] APPARATUS FOR DETERMINING THE REFLECTIVITY OF THE SURFACE OF A MEASURED OBJECT

[76] Inventor: Rolf Bartke, Sybelstrasse 31, D-4000 Düsseldorf, Fed. Rep. of Germany

[21] Appl. No.: 127,462

[22] Filed: Mar. 5, 1980

[30] Foreign Application Priority Data

Mar. 15, 1979 [DE] Fed. Rep. of Germany ....... 2910240

[51] Int. Cl.³ .......................... G01N 21/27; G01J 3/50
[52] U.S. Cl. ..................... 356/407; 356/419; 356/448; 250/238
[58] Field of Search ................... 356/407, 419, 448; 250/238

[56] References Cited

U.S. PATENT DOCUMENTS

| | | | |
|---|---|---|---|
| 3,762,546 | 10/1973 | Keitel et al. | 356/407 X |
| 3,935,463 | 1/1976 | Jacobsen | 250/238 X |
| 3,936,189 | 2/1976 | De Remigis | 356/407 X |
| 3,973,118 | 8/1976 | La Montagne | 356/407 X |
| 4,120,402 | 10/1978 | Swanson | 356/407 X |
| 4,171,918 | 10/1979 | Mactaggart | 250/238 X |
| 4,225,242 | 9/1980 | Lane | 356/407 |

*Primary Examiner*—Vincent P. McGraw
*Attorney, Agent, or Firm*—Owen, Wickersham & Erickson

[57] ABSTRACT

Apparatus for determining the reflectivity of the surface of a measured object, and, in particular, for determining properties of the measured object which are connected with its reflectivity. A light source emits light along a light path so that a wide-band light beam impinges on the surface of the measured object. The light reflected by the surface of the measured object goes through a pair of narrowband light filters which pass, respectively, light beams of different narrow bands of wave-lengths effective for evaluation by a photo-detection device. The photo-detection device comprises two separate photo-detectors each covered by one of the narrow-band filters. The filters are fixed in their positions relative to the photo-detectors and transmit their different wave-lengths of light to their respective photo-detectors.

5 Claims, 2 Drawing Figures

APPARATUS FOR DETERMINING THE REFLECTIVITY OF THE SURFACE OF A MEASURED OBJECT The invention relates to an apparatus for determining the reflective power or reflectivity of the surface of a measured object. In particular, it relates to apparatus for determining the properties of the measured object which are connected with such reflectivity. The apparatus includes a light source which emits light onto the surface of the measured object, a light-receiving device which receives at least the light reflected by the surface of the measured object and conveys it to a photo-detection device for evaluation, and a pair of filter elements which render only light beams of two different narrow bands of wavelengths effective for evaluation by the photo-detection device.

BACKGROUND OF THE INVENTION

An apparatus of the above described type has already been proposed. With that apparatus, light is conveyed from a so-called wide-band light source through a rotating filter plate containing two filters which transmit light of varying wavelengths. Only one light beam of one wavelength is transmitted by each filter plate. This light beam is deflected by means of a passive reflector onto the measured object from the surface of which the light beam is reflected fan-wise. The fan-shaped reflected light is conducted by means of a concave mirror to a photo-detector for evaluation. The two filters are selected as to their transmissivity to light so that the light of one wavelength is absorbed by the irradiated surface of the measured object, while light of the other wavelength is not absorbed. If, for example, humidity on the surface of a solid object is to be measured, then one filter must pass light of a wavelength which is absorbed by water. The wavelength of the light passed by the other filter must be selected so that this light is not absorbed by water. The result of the measurement can then be deduced from the absorption differential of the two light beams.

The disadvantage of the above considered proposed apparatus is that the parameters of the apparatus are not stable and can result in inaccuracies of measurement. Thus, for example, the filters can, under the influence of temperature, undergo changes with regard to the wavelength with which alone they transmit light. The detector used also exhibits a temperature-dependent behavior.

To overcome the above described difficulties, it is already known (German laid-open application No. 28 16 541) in connection with an apparatus of the type considered above, to derive from the wide-band light source a second light beam which is also conducted through the filter plate, but spaced from and parallel with the light beam which is conducted to the measured object. The second light beam is formed alternatingly by light of one wavelength and light of the other wavelength (corresponding to the wavelengths transmitted by the two filters), like the light beam directed onto the measured object. The arrangement is such that, when the light beam directed onto the measured object is formed by light of one wavelength, the second light beam is formed by light of the other wavelength, and vice versa. In this manner, the detector received successively four different light beams. Although evaluation of these four light beams permits elimination of changes in the parameters of the apparatus, this known apparatus also has the disadvantage of relatively high construction costs as well as the use of a driven filter plate.

Starting from an apparatus of the type just described, it has also been proposed to conduct from the wideband light source a single light beam through the filter plate which is in the form of a filter wheel and which, again, is equipped with two filters which transmit light of different wavelengths. The light beam which is being passed through the filter wheel is then formed alternatingly by light of one wavelength and light of the other wavelength. The light beam leaving the filter wheel is then conducted onto a semitransparent mirror which conducts one part of the light onto the measured object and another part of the light onto a reference detector. The light reflected by the surface of the measured object is conducted by means of a concave mirror onto a measuring detector. Thus, the measuring detector and the reference detector receive, alternatingly, light of variable wavelength. The measuring results of the two detectors serve, on the one hand, to evaluate the variable reflection power of the surface of the measured object determined with the two light beams of different wavelength, and, on the other hand, the measuring results serve to eliminate fluctuations in the parameters of the apparatus. Although with this apparatus, light beams of identical wavelength are used simultaneously for measuring and for reference forming, here also the use of a filter plate is a disadvantage because of the resulting relatively high costs of construction.

The underlying object of the present invention is therefore to show a way how an apparatus of the type indicated in the introduction can be constructed with lesser costs than is the case with the above considered devices.

SUMMARY OF THE INVENTION

The problem set out above in connection with apparatus discussed in the introduction is solved in the present invention by having the light source and the light path extending from it to the surface of the measured object are so constituted that a wide-band light beam impinges on the surface, by having the photo-detection device contain two separate photo-detectors, and by having these photo-detectors covered by narrow-band filters which are fixed in their relative position to the photo-detectors and which transmit light of different wavelenghts.

The invention offers the advantage that lower construction costs are involved than in the case of the above considered known and/or proposed devices in determining the reflective power or reflectivity of the surface of a measured object and to determine therefrom in particular the properties of the measured object connected with such reflectivity. In addition, continuous measuring of the measured object is possible in an advantageous manner. It is for example possible, by determining the reflectivity of the surface of an object, to establish its surface humidity. In many substances, such as for example tobacco, timber, flour, milk powder, and the like, and in almost all granular materials, the surface humidity is representative of the total humidity of the substance in question. Determination of the reflectivity of the surface of an object can also be utilized advantageously for determining the fat of a substance, in cases where the fatty layer of the surface of the substance is representative of the total fat content of the substance. This is the case for example with cocoa, milk powder, etc. In the same way, it is possible to determine the protein content of substances, such as for example of wheat and flour. Homogenization of the substance to be examined is however a precondition for an accurate analysis.

If the reflectivity of the surface of solid or liquid objects through which light can penetrate, is to be determined, the measured objects are preferably contained in a light-reflecting carrier. Such objects may, for example, be transparent foils which are to be examined as their humidity content, or they may even be liquids.

The photo-detectors are advantageously disposed directly side-by-side. This results in a particularly simple and compact construction of the apparatus.

It is of advantage to connect the photo-detectors with a cooling device. This offers the advantage of high constancy of the temperature of the photo-detectors.

It is advantageous to also connect the narrow-band filters with the cooling device. This insures in advantageous manner a particularly high temperature constancy during operation of the apparatus.

Advantageously, an electronic analysis device is connected to the outputs of the two photo-detectors. In this analysis device the output signals of the two photo-detectors are compared while supplying corresponding output signals. This offers the advantage that it is possible in a particularly simple manner to process the output signals of the photo-detectors for supplying the corresponding output signals. In the course of the above mentioned comparison the energy of the light received with the one wavelength is then practically correlated with the energy of the light received with the other wavelength, for example by quotient formation. The output signal thereby obtained can be used in indicating the properties connected with the determined reflectivity of the surface of the measured object involved.

As a practical matter, a passive reflector is provided in the light path from the light source to the surface of the object. This results in the advantage of a relatively low height of the structure of the apparatus.

A particularly slight height of the structure of the apparatus is possible if a concave mirror is provided in the light path from the surface of the measured object to the photo-detectors.

The invention is described in further detail by way of example in connection with the drawings.

DESCRIPTION OF A PREFERRED EMBODIMENT

Figure 1:
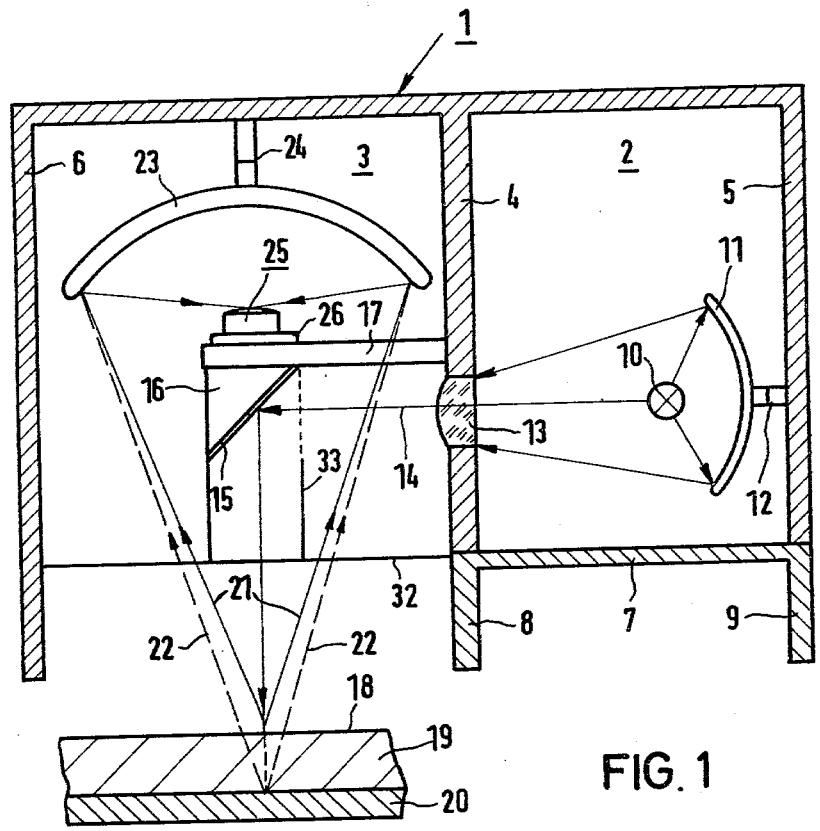
FIG. 1 is a schematic representation in sectional view of an apparatus in accordance with the invention.

FIG. 1 shows an embodiment of apparatus 1 in accordance with the invention. This apparatus 1 comprises substantially a container-like housing with two chambers 2 and 3 into which the space inside the housing is separated by a wall 4. In accordance with FIG. 1, this housing is delimited by two outer walls 5 and 6, respectively. The bottom of chamber 2 is closed off by means of a plate 7 which is connected to two carrier plates 8 and 9.

Inside the chamber 2, there is (schematically indicated) a light source 10 which may for example be a tungsten filament lamp; it may be operated continuously or intermittently. The light source 10 emits wide-band light, that is light made up of many wavelengths. A concave mirror 11 is secured by means of a securing and adjustment device 12 on the wall 5, and light from the source 10 is conducted by means of the concave mirror 11 to a condenser lens 13 located in the wall 4. From the lens 13, a wide-band light beam 14 emerges in the chamber 3.

In the chamber 3 of the housing shown in FIG. 1, a carrier device 17 is secured to the wall 4 and at a lower part thereof a passive reflector 15 is mounted via a securing device 16. The carrier device 17, which is preferably formed by a carrier arm, carries on its upper side a photodetector device 25 which may be mounted, for example, on an evaluation device 26.

In the chamber 3, there is further provided a concave mirror 23 disposed above the photo-detector device 25. This mirror 23 is mounted on the upper side of the illustrated container via a holding and adjustment device 24.

The measured object 19 which is to be analyzed with regard to the reflectivity of its surface 18 is disposed in the region of the open bottom of the chamber 3 of the housing shown in FIG. 1. The chamber 3 is closed off by a transparent plate 32. To avoid disturbing reflections on the plate, the passive reflector 15 is surrounded by a tube 33 which reaches down to said plate 32 and has an opening in direction of the condensor 13. In the event that the object 19 is translucent, the object 19 is received by a reflecting carrier 20.

As will be seen in FIG. 1, the wide-band light beam 14 emerging from the condenser 13 arrives, after deflection and reflection by the passive reflector 15, on the surface 18 of the object 19. From the surface 18 of the object 19 or from the carrier 20, the light beam is reflected fanwise to a greater or lesser degree, towards the passive reflector 23 (either corresponding to the beam path 21 from the surface 18 of the measured object or corresponding to the beam path 22 from the surface of the reflecting carrier 20); and the light beams are conducted by the passive reflector 23 toward the photodetector device 25.

Figure 2:
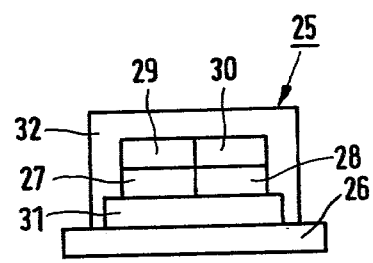
FIG. 2 is a schematic representation on an enlarged scale of a photo-detector device provided for the apparatus in accordance with FIG. 1.

The detailed construction of the photo-detector device 25 is shown schematically in FIG. 2. The photo-detector device 25 contains two photo-detectors 27 and 28 which are disposed directly side-by-side, one of which serving as a measuring detector and the other serving as a reference detector. Each of these two photo-detectors 27 and 28 is covered by a fixed, non-rotating narrow-band filter 29 and 30, respectively, each of which transmits a relatively narrow range of wavelengths. The two narrow-band filters thus transmit light of different wavelengths.

The two photo-electrodes 27 and 28 are connected with a cooling device 31 with which therefore, the narrow-band filters 29 and 30 are also connected. As already mentioned, this cooling device 31 insures operation with a high degree of temperature constancy.

In this connection, it should be noted further that it is the use of the non-rotating narrow-band filters 29 and 30, which are fixedly mounted in their positions relative to the photo-detectors 27 and 28 that makes it at all possible to obtain temperature compensation or temperature constancy.

The electronic analysis device 26 which has already been mentioned in connection with FIG. 1 and which is merely schematically indicated in FIG. 2 is connected by its inputs to the outputs of the two photo-detectors 27 and 28. The electronic analysis device 26 compares the output signals fed to it by the photo-detectors 27 and 28, and thereupon emits the corresponding output signals. In other words, this means that the electronic analysis device correlates the energy levels of light beams of different wavelengths, for example by quotient formation between the energy of the light which has been received by the measuring detector and the energy of the light which has been received by the reference detector. The output signal thus obtained by the analysis device can then be used for determining properties of the measured object which are connected with its reflectivity.

With regard to the detector device shown in FIG. 2, it should further be noted that its detectors 27 and 28, the narrow-band filters 29 and 30, and the cooling device 31 are preferably surrounded by a housing which enables light to impinge on at least from the top onto the photo-detectors 27, 28 through the narrow-band filters 29 and 30. The analysis device 26 which, in FIG. 2, is shown to be below the detector device 25 can also be mounted at another location, for example outside the housing shown in FIG. 1.

To those skilled in the art to which this invention relates, many changes in construction and widely differing embodiments and applications of the invention will suggest themselves without departing from the spirit and scope of the invention. The disclosures and the description herein are purely illustrative and are not intended to be in any sense limiting.

I claim:

1. Apparatus for determining the reflectivity of the surface of a measured object, in particular for determining properties of the measured object which are connected with its reflectivity, comprising light source means for emitting light along a light path onto the surface of the measured object so that a wide-band light beam impinges onto said surface and is reflected therefrom, photo-detection means for evaluation, a concave mirror in the path of the light reflected from the surface of the measured object and focused on the measured object for collecting the reflected light and conveying it to and concentrating it on said photo-detection means, a pair of narrow-band light filters which pass, respectively, light beams of different narrow bands of wavelengths effective for evaluation by the photo-detection means, said photo-detection means comprising two separate photo-detectors immediately adjacent each other, side by side, each covered by one of said narrow-band filters, said filters being immediately adjacent each other, side by side, and directly over their respective photo-detectors fixed in their positions relative to said photo-detectors and transmitting their different wavelengths of light to their respective photo-detectors, and cooling means connected to the photo-detectors and also to said narrow-band filters.

2. Apparatus in accordance with claim 1 having light-reflecting carrier means for supporting solid or liquid measured objects through which light can penetrate.

3. Apparatus in accordance with claim 1 or 2 having an electronic analysis means connected to the outputs of the two photo-detectors for comparing the output signals of the two photo-detectors, and supplying corresponding output signals.

4. Apparatus in accordance with claim 1 having a passive reflector as part of said light path from the light source to the surface of the measured object.

5. The apparatus of claim 1 wherein said photo-detectors are disposed directly on said cooling means, said photo-detectors, filters, and cooling device constituting said photo-detection means being an assembly covering only a small area adjacent to and including the focal point of said concave mirror, whereby the full amount of reflected light can be utilized and the photo-detection device can be quite small and compact.

* * * * *